United States Patent [19]

Tepic et al.

[11] Patent Number: 5,437,666
[45] Date of Patent: Aug. 1, 1995

[54] EXTERNAL FIXATION DEVICE FOR OSTEOSYNTHESIS

[75] Inventors: Slobodan Tepic, Davos, Switzerland; Carel Goslings, Amsterdam, Netherlands

[73] Assignee: Synthes (U.S.A.), Paoli, Pa.

[21] Appl. No.: 119,059

[22] PCT Filed: Aug. 24, 1992

[86] PCT No.: PCT/EP92/01936
§ 371 Date: Sep. 16, 1993
§ 102(e) Date: Sep. 16, 1993

[87] PCT Pub. No.: WO94/04087
PCT Pub. Date: Mar. 3, 1994

[51] Int. Cl.⁶ ............................................. A61B 17/60
[52] U.S. Cl. ............................................ 606/55; 606/54
[58] Field of Search ................ 606/55, 54, 57, 59, 606/58, 56, 72, 73, 90, 104, 105; 602/12, 16, 21

[56] References Cited

U.S. PATENT DOCUMENTS

| | | | |
|---|---|---|---|
| 4,127,119 | 11/1978 | Kronner | 606/56 |
| 4,548,199 | 10/1985 | Agee | 606/55 |
| 4,604,997 | 8/1986 | De Bastiani et al. | 606/55 |
| 4,637,382 | 1/1987 | Walker | 606/55 |
| 4,895,141 | 1/1990 | Koeneman et al. | 606/54 |
| 4,922,896 | 5/1990 | Agee et al. | 606/55 |
| 4,968,316 | 11/1990 | Hergenroeder | 606/90 |
| 5,160,335 | 11/1992 | Wagenknecht | 606/59 |

FOREIGN PATENT DOCUMENTS

| | | |
|---|---|---|
| 248138 | 12/1987 | European Pat. Off. |
| 458486 | 11/1991 | European Pat. Off. |
| 1225559 | 4/1986 | U.S.S.R. ............... 606/55 |
| 1380738 | 3/1988 | U.S.S.R. ............... 606/55 |

*Primary Examiner*—Stephen C. Pellegrino
*Assistant Examiner*—Guy Tucker
*Attorney, Agent, or Firm*—Davis Hoxie Faithfull & Hapgood

[57] ABSTRACT

The external fixation device for osteosynthesis is made up of first and second longitudinal bars (3,4) as carriers for fixation elements (5;10) to the bone (7), a three-dimensional shell (1) attached to the extremity of said first bar (4) and a gliding element (2) attached to the extremity of said second bar (3) having at least three gliding points on each side of said shell (1). The gliding element (2) can consists of a first disk (2A) gliding on one side of the shell (1) and a second disk (2B) gliding on the opposite side of the shell (1), both disks (2A,2B) being connected through a central hole (12) in the center of the shell (1) by a threaded extension (2C).

The shell (1) and the gliding element (2) are movably arranged to each other in such a way that the free ends of the bars (3,4) are extending in opposite directions.

The device enables motion of the wrist joint about all three axes, while keeping the center of rotation at one point during treatment of the fracture and thus preventing complications.

11 Claims, 6 Drawing Sheets

EXTERNAL FIXATION DEVICE FOR OSTEOSYNTHESIS

FIELD OF THE INVENTION

This invention relates to an external fixation device for osteosynthesis, in particular for the treatment of distal radius fractures.

BACKGROUND OF THE INVENTION

Distal radius fractures are among the most common encountered fractures in emergency departments of hospitals. Usually they are referred to as Colles or Pouteau fractures. The frequency of report is about 10% of all fractures. The most common cause of this fracture are a fall on the outstretched hand, a fall from height and motorvehicle accidents. The classic method of treatment is closed reduction of the fracture and plaster cast support. However, plaster cast is only sufficient for fractures with no or little displacement and/or comminution. Other treatment possibilities include open reduction and plate osteosynthesis, functional bracing and external fixation. External fixation is mainly applied in comminuted, intra-articular and/or unstable fractures. The management of distal radius fractures by means of external fixation is based on the principle of ligamentotaxis. This means that when a force is applied across a joint (e.g. the wrist) by distraction, the capsule and ligaments of the joint are placed under tension and thus tend to maintain the reduction of the adjacent bone fragments.

The conventional external fixation devices consist of a rigid frame built up from two proximal pins (e.g. Kirschher wires) in the radius and two distal pins in the second and/or third metacarpal, connected by one or more cross bars. Since this configuration of the frame crosses the wrist joint, no movement of this joint is possible in presence of the external fixator. This can result in severe complications like post-traumatic joint arthrosis, reflex sympathetic dystrophy (Sudeck's dystrophy) and osteoporosis, leading to impairment of wrist function and further morbidity.

From EP-A1 0 458 486 RICHARDSON a bone fixator frame is known which allows relative rotation of the bone segments in two axes. Similar single axis frames have been used for the fixation of radius fractures. These known fixators do not allow for physiological range of movement and require less than optimal surgical approach.

SUMMARY OF THE INVENTION

In accordance with the invention an external fixation device is provided which will enable e.g. motion of the wrist joint about all three axes, while keeping the center of rotation at one point during treatment of the fracture and thus preventing the above mentioned complications.

The device comprises a first and a second longitudinal bar as carrier for fixation means to the bone, a three-dimensional shell attached to the extremity of said first bar and a gliding element attached to the extremity of said second bar, whereby said shell and said gliding element are movably arranged to each other in such a way that the free ends of said first and second bars are extending in opposite directions.

The three-dimensional shell may have an ellipsoid or any other suitable three-dimensional shape but preferably has the shape of a spherical zone.

The gliding element needs at least three gliding points on each side of the shell, preferably it consist of a first disk gliding on one side of the shell and a second disk gliding on the opposite side of the shell, the first and second disks being connected through a central hole in the center of the shell. Most preferably the first and second disks are provided with an annular gliding area for contacting the shell.

The two disks of the gliding element can either be fixed exchangeably or permanently to each other. Preferably the first and second disks are connected by means of screw threads allowing releasable relative positioning of said disks to said shell.

In another aspect the invention comprises a third longitudinal bar releasably fixed and running parallel to said first and second longitudinal bars, which is to be used only temporarily to immobilize the fixator and the joint.

While a number of metals can be used to construct the external fixation device according to the invention, aluminium is the preferred choice due to its relatively low radiopacity; low friction surface treatments are also possible on aluminium. Alternatively fiber reinforced polymers can be used for the device.

DESCRIPTION OF THE DRAWINGS

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

In the drawings.

DETAILED DESCRIPTION OF THE INVENTION

Figure 1A:
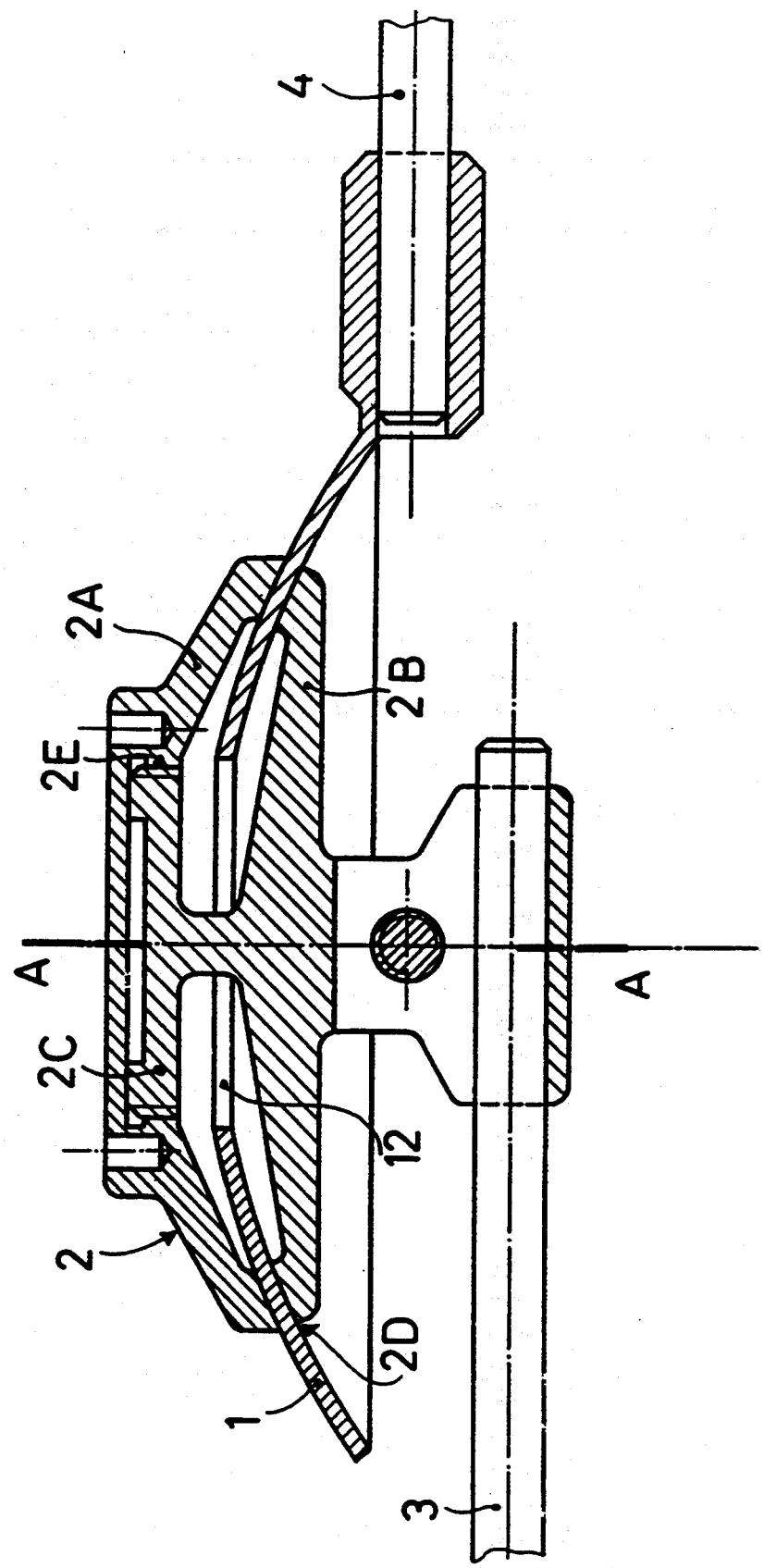
FIG. 1a is a section through the device in accordance with the invention.

The device as shown in FIG. 1a consists basically of two parts 1,2 glidingly connected to each other. The first part consists of a three-dimensional shell 1 having the shape of a spherical zone with the radius R. The second part is a gliding element 2 consisting of a first disk 2A and a second disk 2B having an annular gliding contact area 2D and being linked together by a threaded extension 2C.

Alternatively to a full annular contact area 2D the disks 2A and 2B could be provided with gliding pads to contact the shell 1, whereby at least three of such pads should be present on each side of the shell 1.

The first disk 2A is mounted on top of the shell 1 and the second disk 2B is mounted below on the opposite side of the shell 1. The threaded extension 2C of the disk 2B passes through the opening 12 of the shell 1 and is secured in the threaded hole 2E in the center of the first disc 2A. By means of the threaded extension 2C it is possible to adjust the gap between the annular gliding contact areas 2D and the shell surface and thereby allow for free motion between the two parts.

Figure 1B:
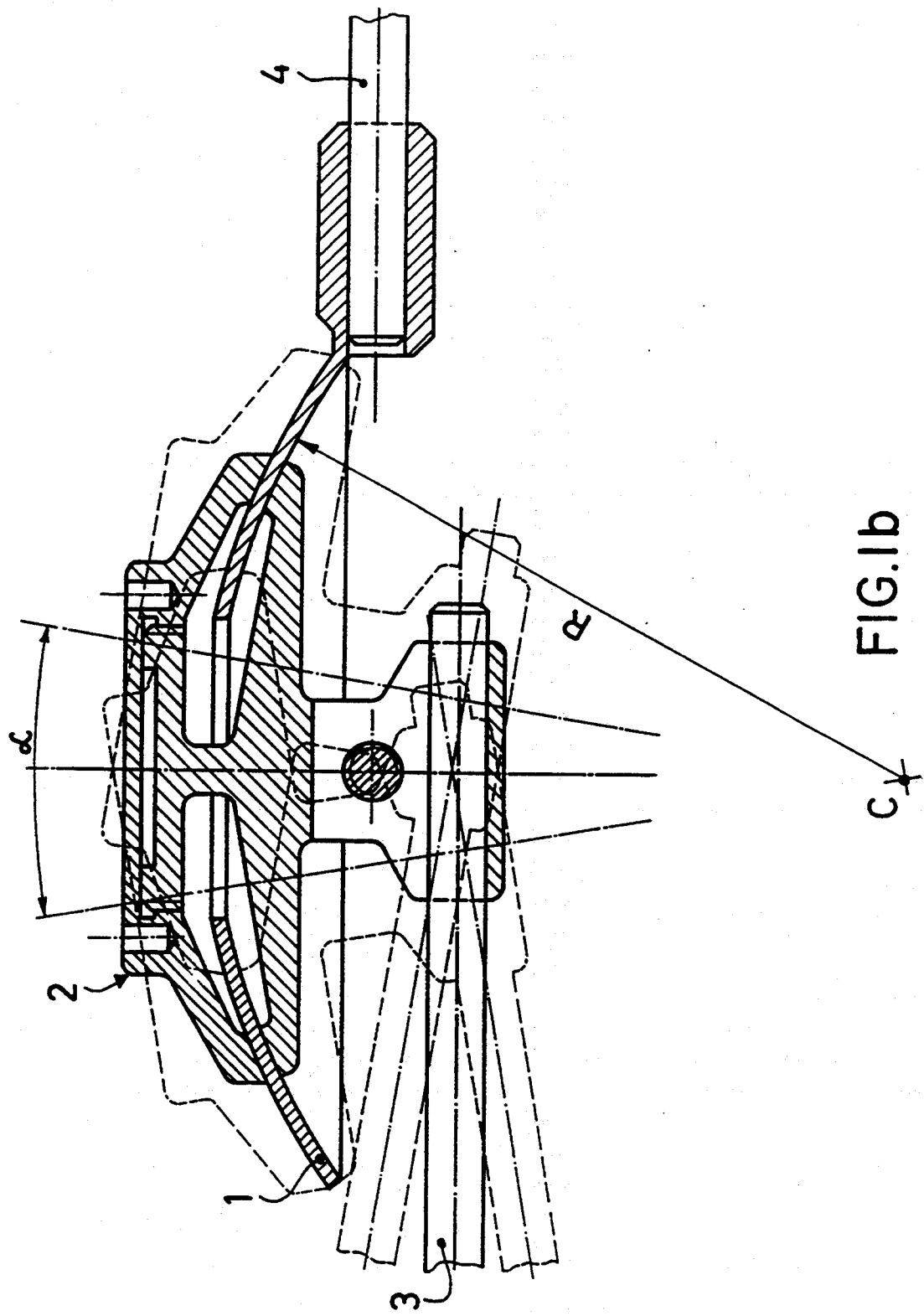
FIG. 1b is a section through the device according to FIG. 1a showing the range of rotation of the device.

FIG. 1b shows the range of rotation α in the plane parallel to the longitudinal bars 3,4. The center of rotation is at C, with radius of the shell 1 marked by R.

Figure 1C:
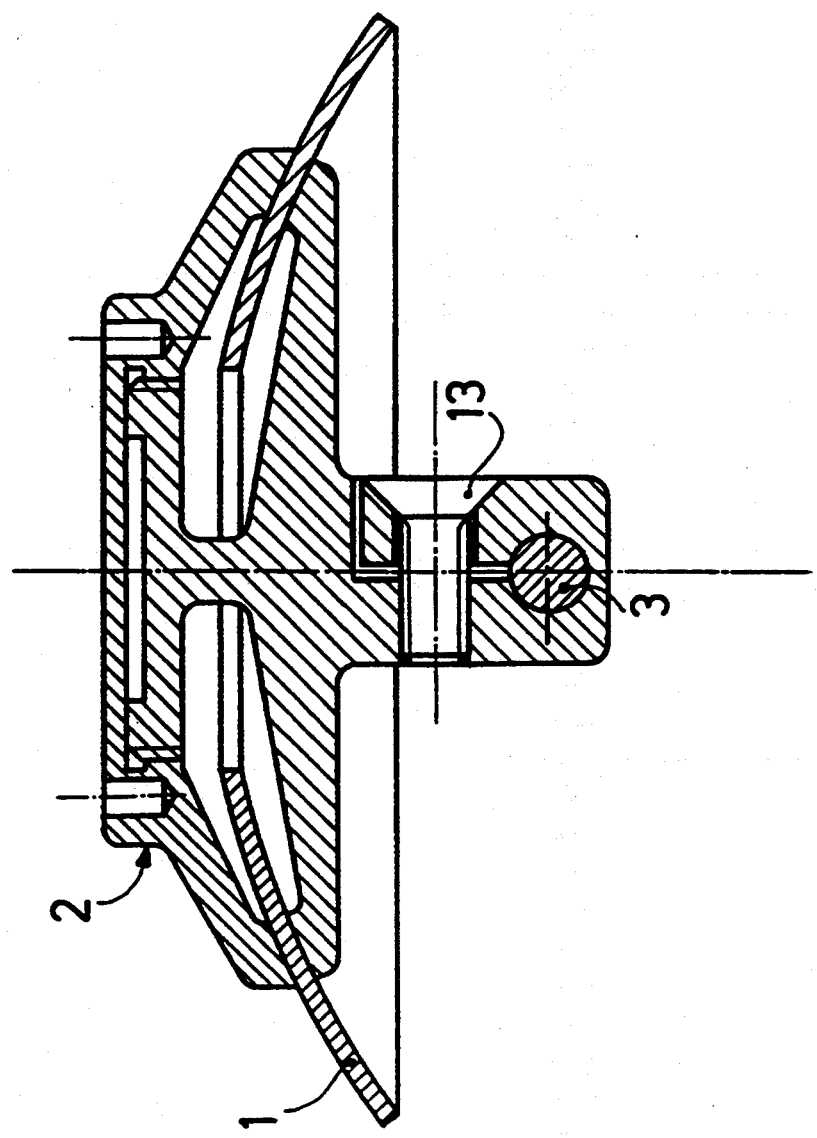
FIG. 1c is a section perpendicular to that according to FIG. 1a along line A—A.

FIG. 1c shows a vertical section along the line A—A of FIG. 1a. The screw 13 is used to clamp the gliding element 2 of the device to the longitudinal bar 3.

Figure 2:
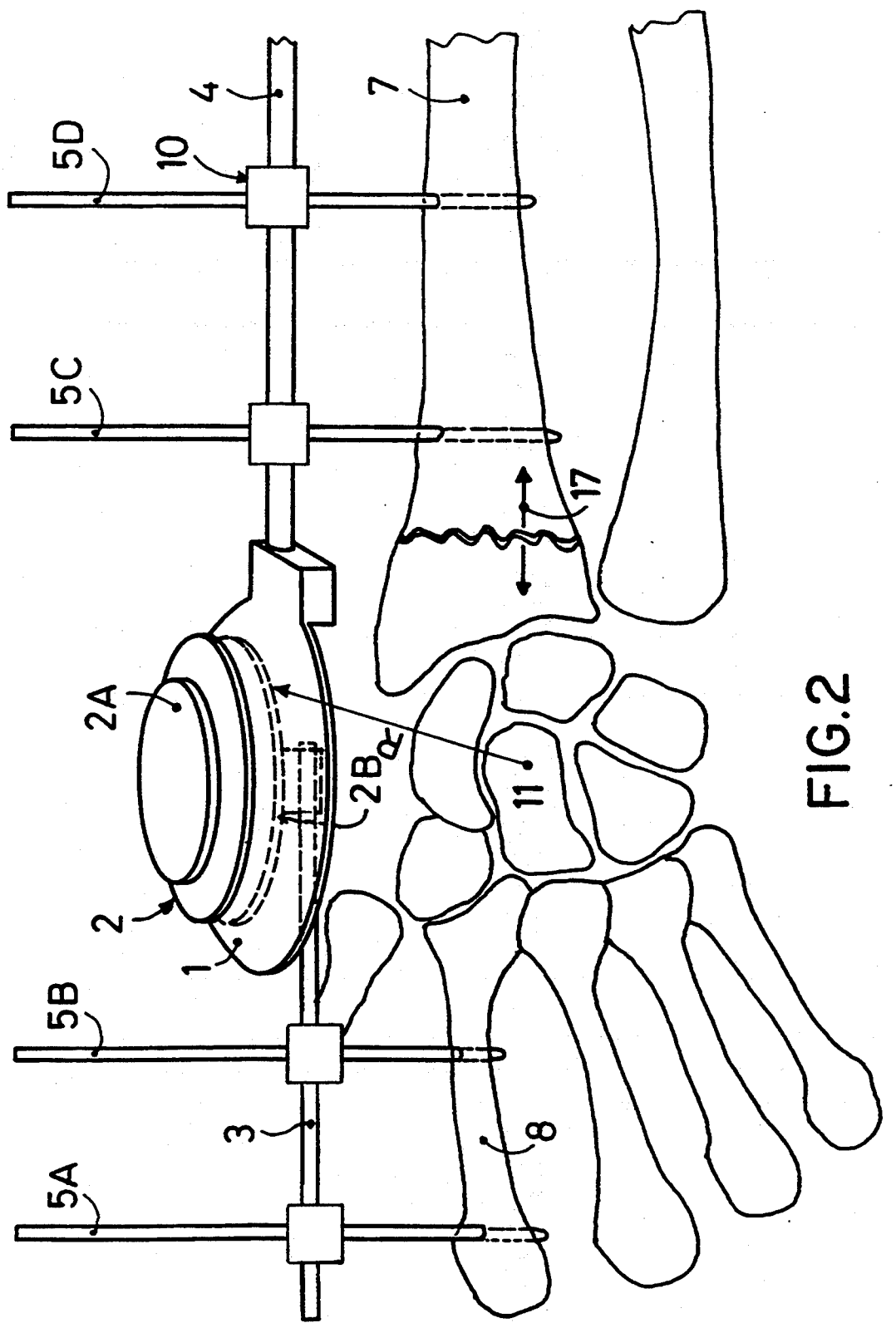
FIG. 2 is a side view of the device in accordance with the invention applied to a distal radius fracture.

The shell 1 is attached to the extremity of the first longitudinal bar 4 and the gliding element 2 is attached to the extremity of a second longitudinal bar 3 which act as carriers for fixation means 5,10 to the bone as shown in FIG. 2. The shell 1 and the gliding element 2 are movably arranged to each other in such a way that the free ends of said first and second longitudinal bars are extending in opposite directions as shown in FIG. 2. This results in a fixation device having a center of rotation in the center of a sphere, i.e. at a distance R from the spherical zone surface of the shell 1.

As shown in FIG. 2 the external fixation device can be mounted at the wrist by means of four Kirschner wires 5A,5B,5C,5D held by conventional external fixation clamps 10 to the longitudinal bars 3,4. Two Kirschner wires 5A,5B are fixed to the second metacarpal 8 and two further Kirschner wires 5C,5D are fixed to the radius 7.

The device is mounted in such a way that the spherical zone surface of the shell 1 is located approximately at a distance R from the center of rotation of the wrist joint 11. By this measure the external fixation device provides a means of maintaining fracture alignment and distraction as marked by arrow 17, while allowing rotation of the wrist joint in all planes.

Figure 3:
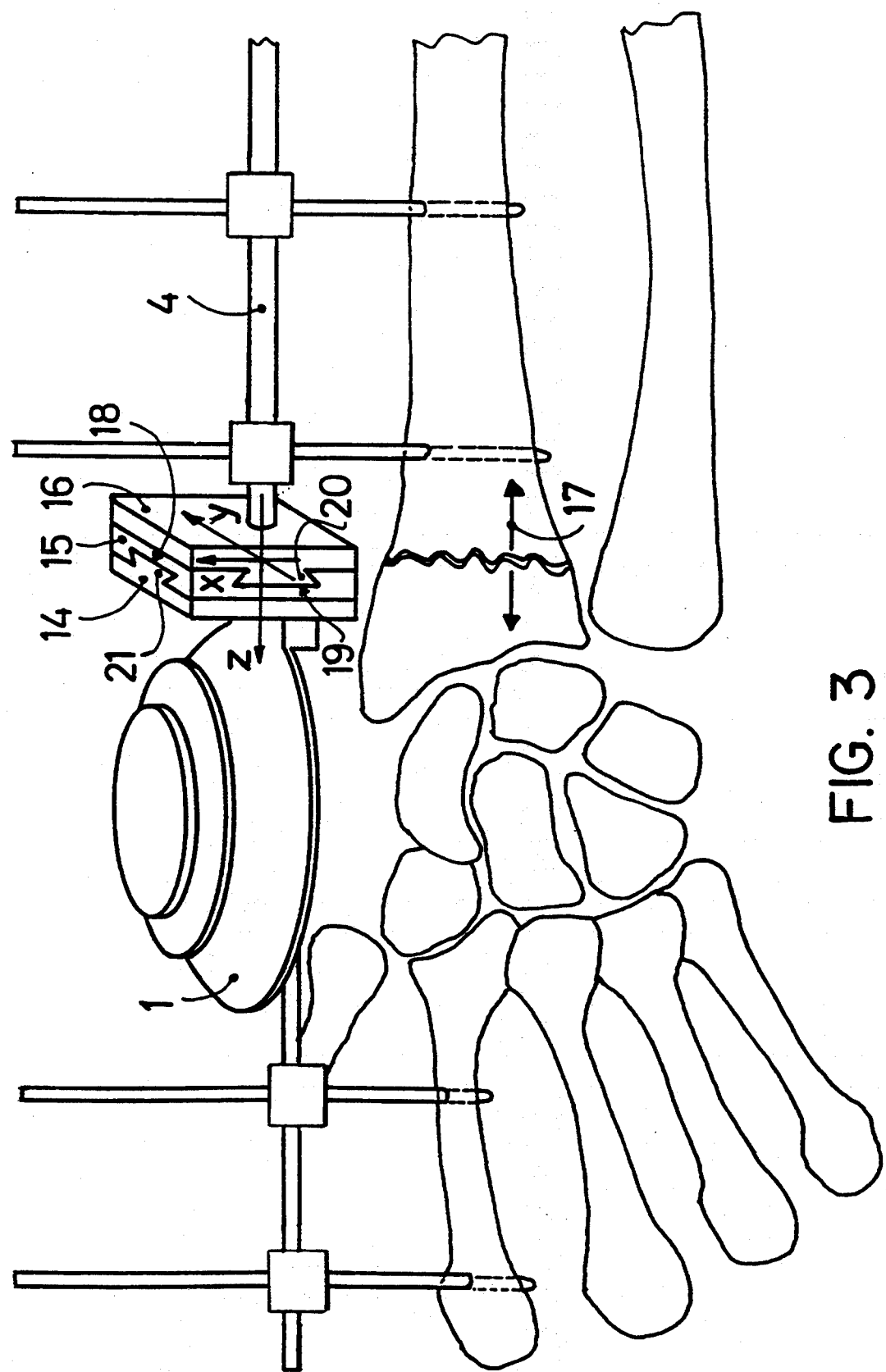
FIG. 3 is a side view of a modified device allowing additional translational movements.

FIG. 3 shows an embodiment of the invention with an additional set of elements 14,15,16 interposed between the shell 1 and the longitudinal bar 4 which allows for free translation between them along the axes x and y. This is done e.g. by having a guiding element 15 with gliding dovetail grooves 18,19 extending at 90° to each other interposed between gliding elements 14 and 16 with matching dovetail pairs 20,21. Gliding elements 14 and 16 may be fixed to the guiding element 15 by any type of known fixation means, e.g. fixation screws, which are not shown in the drawing. By this construction only one degree of freedom is restricted—the z-axis translation. Thus, the external fixation device can be used to generate distraction 17 at the fracture site without restraining movements of the wrist.

Figure 4:
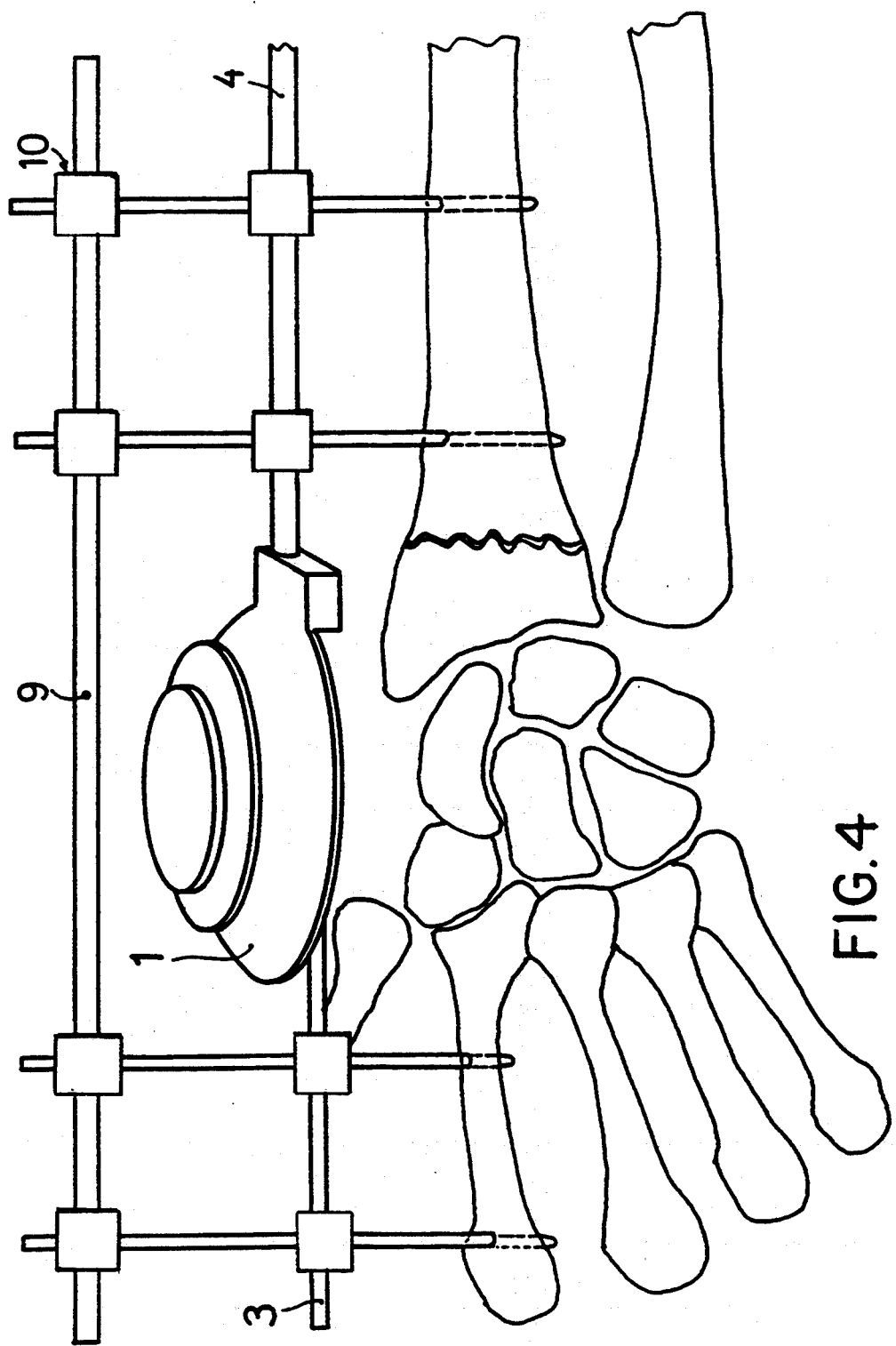
FIG. 4 is a side view of the device according to FIG. 2 with an additional cross bar.

The sliding movability between the shell and the gliding elements of the external fixation device according to FIGS. 1 to 3 can be prevented either by tightening the threaded connection 2C between the two disks 2A,2B or as shown in FIG. 4 by a third longitudinal bar 9 running parallel to the first and second longitudinal bars 3,4, to which the four Kirschner wires 5A,5B,5C,5D are fixed by additional external fixation clamps 10.

What is claimed is:

1. External fixation device for osteosynthesis comprising:
   a first longitudinal bar,
   a second longitudinal bar,
   means on said first and second longitudinal bars for attaching bone fixation devices to said bars,
   a three dimensional arcuate shell attached to an extremity of said first bar,
   a gliding element attached to an extremity of said second bar,
   said gliding element having a recess to retain said shell while permitting relative arcuate movement between said element and said shell, and
   means connecting said first longitudinal bar to said shell for allowing free translation between said first longitudinal bar and said shell along perpendicular axes which are orthogonal to said first longitudinal bar.

2. External fixation device according to claim 1, wherein said shell has the shape of a segment of a sphere.

3. External fixation device according to claim 2, wherein said shell is provided with a central hole through which said gliding element extends.

4. External fixation device according to claim 3, wherein said gliding element comprises a first disk gliding on one side of said shell and a second disk gliding on the opposite side of said shell, said first and second disks being connected through said central hole.

5. External fixation device according to claim 4, wherein said first and second disks are provided with an annular gliding area for contacting said shell.

6. External fixation device according to claim 5, wherein at least said gliding area is made of aluminium.

7. External fixation device according to claim 4, and comprising fixation means connecting said first and second discs and allowing releasable positioning of said disks relative to said shell.

8. External fixation device according to claim 1, wherein said first and second longitudinal bars are releasably fixable to a third longitudinal bar parallel to said first and second longitudinal bars.

9. External fixation device according to claim 1, wherein all parts are made of aluminium.

10. An external fixation device according to claim 1 wherein said means for allowing free translation is a connecting block joining said first longitudinal bar to said shell, said block having a first element connected to said first longitudinal bar and capable of displacement along a first axis perpendicular to the longitudinal axis of said bar and a second element connected to said shell and capable of displacement along an axis perpendicular to the longitudinal axis of said bar and to said first axis.

11. An external fixation device for osteosynthesis comprising:
   a first longitudinal bar,
   a second longitudinal bar,
   means on said first and second longitudinal bars for attaching bone fixation devices to said bars,
   a three dimensional arcuate shell connected to an extremity of said first bar,
   a gliding element connected to an extremity of said second bar,
   said gliding element having a recess to retain said shell while permitting relative arcuate movement between said gliding element and said shell, and
   a block connecting said first longitudinal bar to said shell, said block having a first element connected to said first longitudinal bar, a second element connected to said shell and a guide having a plurality of dovetail grooves extending at 90° to one another, said first and second elements having tongues for engagement in said dovetail grooves, enabling said shell and said first longitudinal bar to be displaced orthogonaly relative to one another.

* * * * *